United States Patent [19]
Meddings et al.

[11] Patent Number: 5,605,840
[45] Date of Patent: Feb. 25, 1997

[54] METHOD FOR THE DETECTION OF GASTRIC EPITHELIAL DAMAGE

[76] Inventors: Jonathan B. Meddings, 16 Varshaven Place NW., Calgary, Canada, T3A 0E1; Lloyd Sutherland, 500 Eau Claire Ave., Calgary, Canada, T2P 3R8; John L. Wallace, Site 5 R.R. #1, Cochrane, Canada, T0L 0W0

[21] Appl. No.: 456,203

[22] Filed: May 31, 1995

Related U.S. Application Data

[62] Division of Ser. No. 190,139, Feb. 3, 1994, abandoned.

[30] Foreign Application Priority Data

Sep. 18, 1991 [CA] Canada .................................... 2051787

[51] Int. Cl.$^6$ .................................................. G01N 31/22
[52] U.S. Cl. .............................. 436/94; 436/64; 436/811; 436/813
[58] Field of Search ................... 436/94, 95, 63, 436/64, 811, 813; 422/61

[56] References Cited

U.S. PATENT DOCUMENTS

| | | | |
|---|---|---|---|
| 3,368,872 | 2/1968 | Natelson | 436/95 |
| 5,023,072 | 6/1991 | Cheng | 424/9 |

*Primary Examiner*—Lyle A. Alexander
*Attorney, Agent, or Firm*—Fitzpatrick, Cella, Harper & Scinto

[57] ABSTRACT

Disclosed is a method for the detection of gastric epithelial damage and a method which is performed by administering a disaccharide to a patient, assaying the patient's blood or urine for the presence of the disaccharide and correlating the determined disaccharide assay value to gastric epithelial damage.

3 Claims, 7 Drawing Sheets

METHOD FOR THE DETECTION OF GASTRIC EPITHELIAL DAMAGE

This application is a DIVISIONAL Application of application Ser. No. 08/190,139, which has a Feb. 3, 1994 now abandoned, date under 35 USC §371(f).

BACKGROUND OF THE INVENTION

The invention herein is directed to a method for the detection of gastric epithelial damage and more particularly, is directed to a method for the detection of ulcers and lesions in the stomach using non-invasive, non-radioactive and non-x-ray techniques or procedures. The method herein is useful in detecting and diagnosing gastric epithelial damage regardless of the cause for such damage. The method herein is further advantageous in that the method is site specific for damage to the gastric epithelium.

Stomach ulcers can pose a serious health threat as in many instances ulcers are asymptomatic. Since stomach ulcers can develop and be present without any symptoms, the damage brought about by the ulcers to the stomach and the bleeding associated with such ulcers can be a serious health risk. The health risk can prove to be fatal.

It would be highly desirable to develop a non-invasive and accurate method for detecting and diagnosing the presence of stomach ulcers. The detection and accurate measurement of abnormal mucosa in the stomach such as damage to gastric epithelial cells would be highly desirable. Such a method could be used to diagnose and detect various disorders which cause damage to the stomach epithelial cells. Illustrative disorders are gastric (stomach) ulcers, carcinoma, benign lesions and the like. Stomach ulcers can also occur through the use of non-steroidal anti-inflammatory drugs (NSAIDs) which have as a class been acknowledged by the U.S. Food and Drug Administration as presenting a serious health risk for causing stomach ulcers. The FDA has imposed a warning on labeling for NSAIDs advising users of the attendant risk for ulcers brought about by the constant use of NSAIDs.

Currently there are various methods available for detecting stomach ulcers. The currently employed method with the most reliability is that of performing endoscopies of the patient's stomach. In such a procedure, an endoscope is passed through the esophagus and into the patient's stomach. Such a procedure is discomforting but does allow visual inspection of the stomach lining. The procedure requires some anesthetizing of the patient. Drawbacks of the procedure include discomfort, the anesthetizing of the patient and that it is dependent on the skill of the physician in performing the endoscopy to ensure complete review of the stomach for lesions and in recognizing lesions. This procedure does not lend itself to performance in the physician's office but must be performed generally in a clinic or hospital.

Another procedure that is used is that of using a barium meal administered to a patient which is followed by x-ray examination. Such a procedure has disadvantages in that it does utilize x-rays and requires a learned and skilled evaluation of the resultant x-rays.

Other procedures which have been used enlist the aid of a detecting agent which is radiolabeled and which has an affinity for the lesion in the stomach. By administering the detecting agent, then subsequently monitoring for the presence of the radioisotope, ulcers can be detected. A disadvantage with such a methodology is that it requires the use of radioisotopes. The handling, use and disposal of radioisotopes requires licensing and can present environmental problems. Again the procedure does not lend itself to practice in a physician's office.

It would be desirable to provide a method to detect and diagnose for the presence of stomach ulcers and other lesions in a non-invasive manner which method could be readily used by the practitioner in a simple setting (such as an office) to identify the presence of damage to the stomach epithelial cells. Such a procedure would be helpful in early diagnosis and thereby early treatment of a serious condition. Such a procedure could be easily performed on patients at risk or susceptable to stomach ulcers to detect and treat the damage with the pharmaceuticals armorarium.

SUMMARY OF THE INVENTION

The invention herein is directed to a method for the detection of gastric epithelial damage in a patient. The method provides a non-invasive method for the detection of gastric epithelial damage. The method uses a disaccharide which can be orally administered to a patient and which does not transport across the cell membrane and which is metabolized within the small intestine to its monosaccharides and which disaccharide is not broken down elsewhere in the body. Exemplary disaccharides include sucrose, maltose and lactose.

The method is practiced by administering the disaccharide to a patient, then assaying for the presence of the disaccharide in either the blood or urine of the patient. A value determined in the assay which is greater than a normal control value for the disaccharide in the blood or urine is indicative of gastric epithelial damage.

Further, the method can be practiced by administering the disaccharide to the patient, collecting a blood sample or the urine output of the patient, and assaying the collected blood or urine for the presence of the disaccharide. The assay value for the disaccharide detected in the blood or urine can be correlated to the extent of gastric epithelial damage.

BRIEF DESCRIPTION OF THE DRAWINGS

The invention herein will be better understood with regard to the following detailed description and the accompanying drawings wherein.

DETAILED DESCRIPTION OF THE INVENTION

The invention herein is directed to a method for the detection of gastric epithelial damage. The method can be used to detect lesions in the stomach such as ulcers, including ulcers caused by the administration of NSAIDs. The method is site specific for lesions in the stomach.

The method herein uses a disaccharide which has a native weight of about 342, is highly water soluble, but which is not transported across cell membranes. That is, the disaccharide is not characterized as capable of being transported across cell membranes. The disaccharide is a disaccharide which is not metabolized in the stomach but which is metabolized or otherwise broken down in the lower intestine to its monosaccharides. The disaccharide is not broken down elsewhere in the body which thus enables its detection in the blood or urine of the patient.

It has been found herein that the acceptable and preferred disaccharides are sucrose, maltose and lactose. The most preferred disaccharide is sucrose. Each of the preferred disaccharides is naturally-occurring and can be administered to an animal without any deleterious side effects. Sucrose is an especially preferred disaccharide as it is readily available and can be readily administered to a patient. Sucrose is easy to ingest and can be administered in solid or liquid form in the practice of the method. For the purposes of the practice of the method herein, the disaccharide can be administered in any form suitable and acceptable for oral delivery. As is readily understood by one having skill in the art, the physical form of the disaccharide administered to a patient in the method herein is not critical.

In the practice of the method herein, the disaccharide is orally administered to a patient such that the disaccharide enters the patient's stomach. The disaccharides useful in the practice of the method herein do not generally transport across the cell membrane and therefore are not absorbed by the body from the stomach. The disaccharides that are useful herein generally pass through the stomach of the gastrointestinal tract into the small intestine wherein the disaccharides are metabolized to their monosaccharide components. The monosaccharide units are then absorbed. It is an important aspect of the present method that the disaccharides do not generally transport across the cell membrane in any appreciable amount (microgram quantities may be found in urine as is stated later herein) and that the disaccharides are broken down after leaving the stomach. It is these properties which permit the disaccharides to be employed as markers of gastric epithelial damage of the stomach. The disaccharides are capable of passing through the damaged epithelium into the blood stream of the patient in which they would not be expected to be found absent the presence of epithelial damage.

It has been found herein that, if lesions are present in the stomach, the disaccharides, once administered and present in the stomach, can pass through the openings in the gastric epithelium and enter the blood. Once in the blood stream of the patient, the disaccharides are not metabolized in any of the organs but are cleansed and filtered from the blood whereupon they can be evacuated from the patient in the patient's urine. As the disaccharides are present in the patient's blood and urine, the blood and urine provide suitable media for collection and subsequent assay for the presence of the disaccharides.

It has been found herein that the extent of disaccharide present in the blood is directly related to the extent of gastric epithelial damage. That is, the greater the damage, the greater the passage of disaccharide from the stomach into the patient's blood.

The invention herein can be practiced by orally administering the disaccharide to a patient. In a particularly preferred practice of the method herein, the patient can fast for a sufficient amount of time, such as six to twelve hours or six to eight hours, prior to ingesting or administering the disaccharide. The method is practiced by administering a known amount of disaccharide. It is desirable to administer a sufficient amount of disaccharide as to facilitate its susequent recovery and assay. However, the amount of disaccharide administered is not critical as the presence of sucrose in the urine or blood of a patient is an indicator of the presence of some gastric epithelial damage. Following the administration of the disaccharide, the patient's total urine output can be collected over a period of time. The total urine output can be collected for up to twenty-four hours. It has been found herein that the urinary collection can be from the first evacuation of the patient up to two to five hours thereafter. As will be described hereinafter, the total urine output of a patient up to five hours after administration of the disaccharide has proven to be an effective and sufficient amount of time for detecting the disaccharide in the urine.

Alternatively, a blood sample can be taken from the patient within a selected time following administration of the disaccharide. A suitable amount of time can be from 30 minutes to about 2 hours following administration of the disaccharide in which a blood sample can be taken from the patient. The collected urine or blood can then be assayed for the presence of sucrose. Any suitable assay technique can be followed. That is, any standard or customary assay procedure for sucrose in either blood or urine can be used. It is preferable that the assay be a quantitative assay so that the amount of disaccharide determined in the results can be correlated to the extent of gastric epithelial damage. A qualitative assay can be predictive of some epithelial damage. A qualitative assay having an indicator threshold level prior to indicating the presence of the disaccharide can be performed as a quick diagnostic tool for determining whether further evaluation or testing of a patient should be performed.

It has been found herein that all human urine contains measurable amounts of sucrose in the concentration range of 0.1–1 µg/µl. Presumably this represents dietary sucrose that normally permeates across the gastric mucosa and is excreted in the urine.

In the practice of the method herein the disaccharides are the preferred compounds as they have the acceptable water solubility properties, safety and are non-metabolizable in either the stomach, blood or urine of the patient and they can be readily detected qualitatively and quantitatively in the blood or urine. Further, the disaccharides are acceptable as they are destroyed by the digestive process in the small intestine. As the disaccharides are destroyed by the digestive process in the small intestine, they provide no indication of lesions in the intestine but rather are site-specific for lesions or gastric epithelial damage in the stomach. The disaccharide compounds are acceptable as they are sugars which are native to the daily diet and that are metabolized within the small intestine to monosaccharides. They all have a molecular weight of around 300, are highly water soluble, are not transported across cell membranes and are not broken down elsewhere in the body. Normally these compounds are rapidly degraded to glucose and other monosaccharides within the proximal small intestine. Thus, if sucrose (ordinary table sugar) is found in either blood or urine in its native form, it must have crossed the gut proximal to the small intestine.

With increasing damage to the epithelium, there is greater final concentration of the disaccharide in the plasma of the patient. The disaccharides, and specifically sucrose, represents a unique indicator for determination of gastric epithelial damage as it has several properties that make it exceedingly attractive for detection of chronic damage, especially in man. The disaccharides and especially sucrose are unlikely to be viewed as harmful agents when used in man.

The efficacy of the methodology herein has been tested in both animal and human studies. The method herein was validated in an animal model of acute NSAID-induced gastric damage in the rat and rabbit.

BIOLOGICAL EXPERIMENTALS

Acute NSAID-Induced Gastric Damage in the Rat

Figure 1:
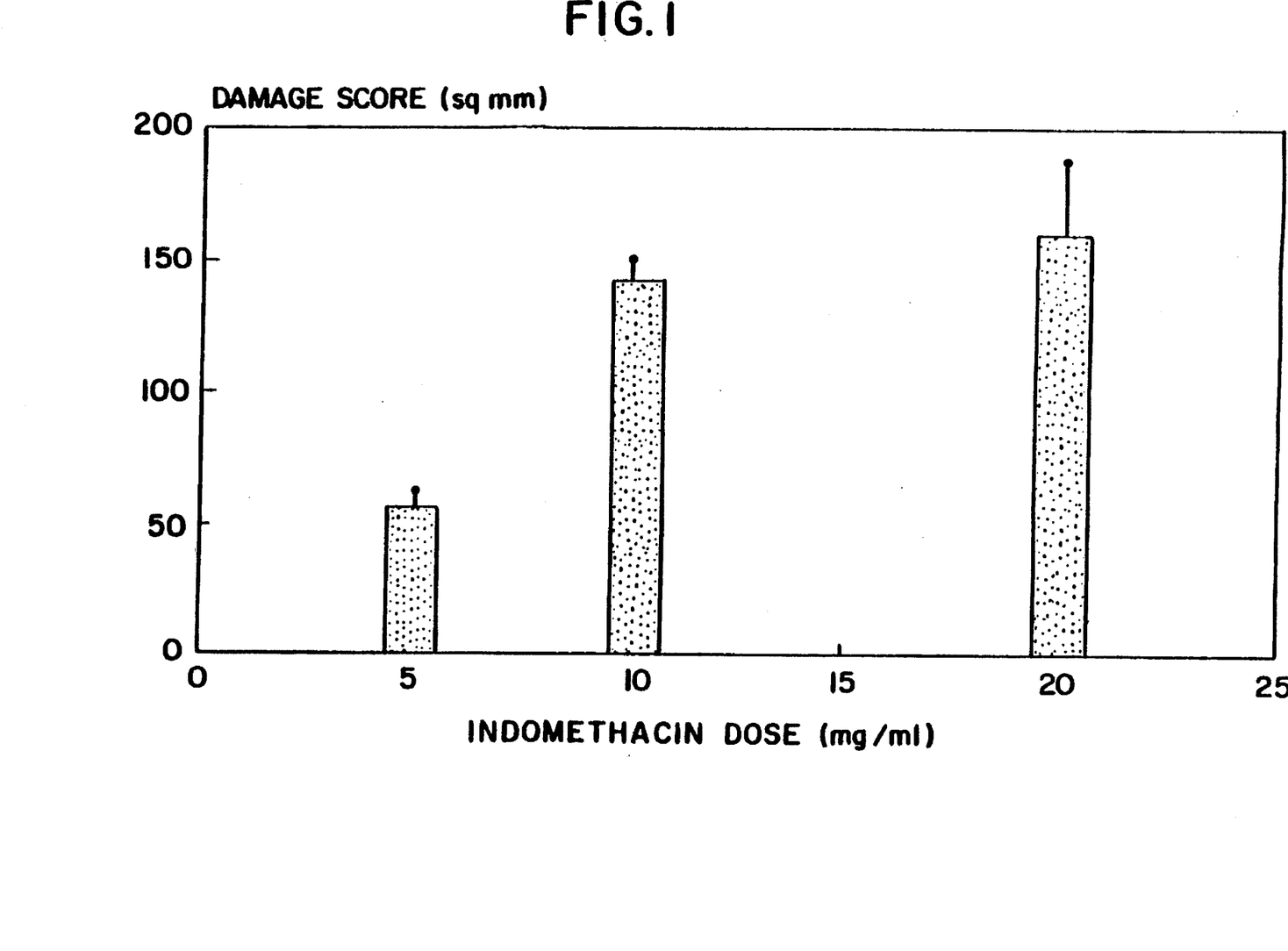
FIG. 1 is a bar graph representing the gastric damage in the rat as a function of the intraluminal concentration of indomethacin.

A model was developed to detect acute NSAID-induced gastric damage in the Sprague-Dawley rat. Following anesthesia, the abdomen is opened and catheters placed into the stomach through both the pylorus and esophagus. The gastric contents are carefully washed out and the lumen profused with saline. Following this, indomethacin (NSAID) or vehicle is introduced and allowed to sit for thirty minutes. Subsequently, the NSAID is removed and replaced with 100 mM HCl for sixty minutes. Such studies produce rapid and extensive superficial damage to the rat's stomach very similar to the acute NSAID lesions observed in man. Furthermore, the damage is reproducible and dose-dependent. A clear gradient of gastric damage can be produced with indomethacin concentrations ranging from 0–20 milligrams/mL. Throughout the procedure the animal remains anesthetized. FIG. 1 is a bar graph illustrating the results of such a study which shows the dependency of gastric damage on the intraluminal concentration of indomethacin. Damage was quantitated as the gastric surface area involved macroscopically with erosions or acute ulcerations. Each point represents the mean plus or minus the standard error for 5–10 animals.

Figure 2:
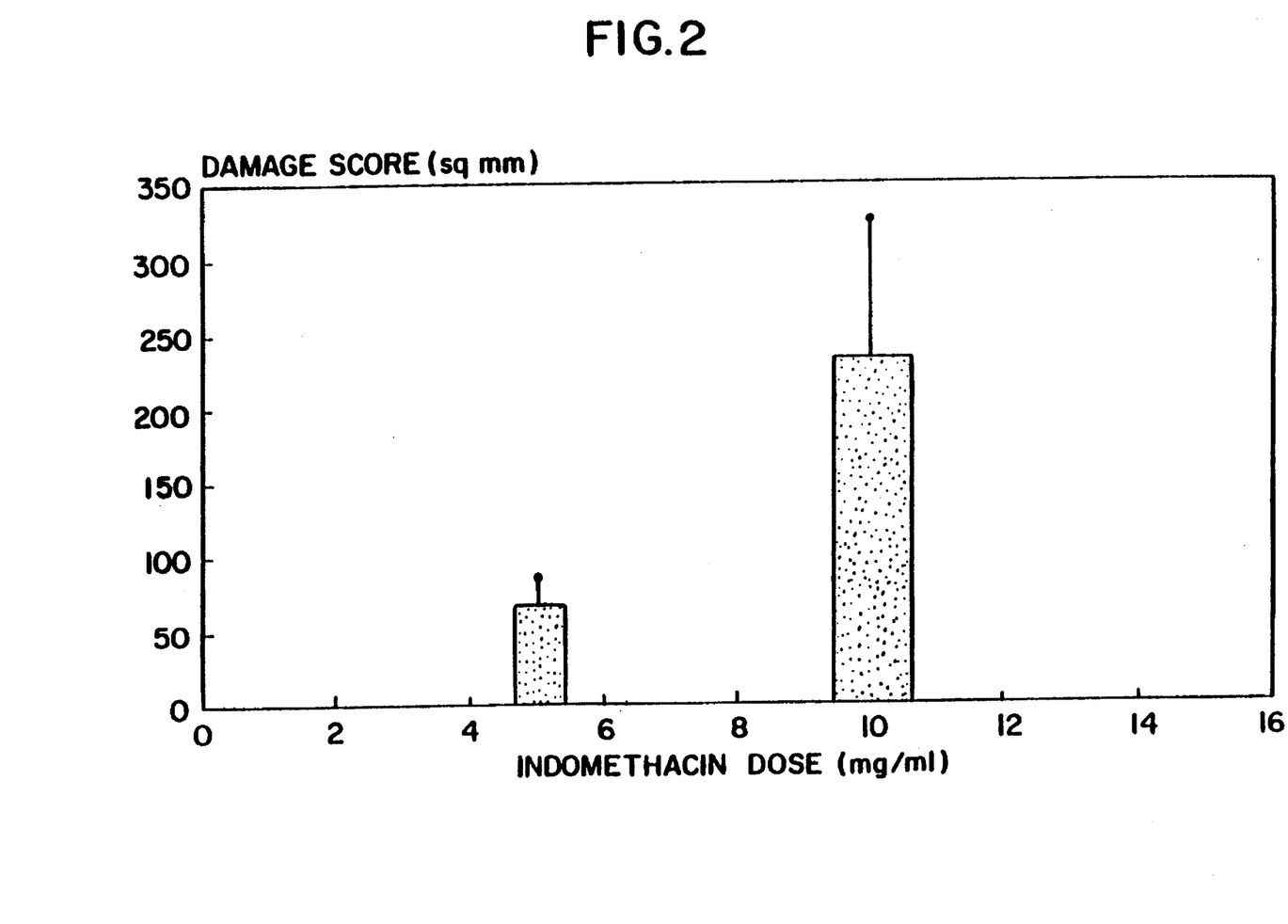
FIG. 2 is a graph illustrating the sensitivity of the rabbit stomach to indomethacin.

It was found herein that the same biological model was applicable when performed in New Zealand white rabbits as a similar response to intraluminal indomethacin emerged where an increasing luminal concentration of indomethacin produced an increasingly severe pattern of damage. The results are shown in the bar graph illustrated in FIG. 2. The damage was quantitated as the gastric surface area involved macroscopically with erosions or acute ulceration. Each point represents the mean plus or minus the standard error for 4–10 animals.

Figure 3:
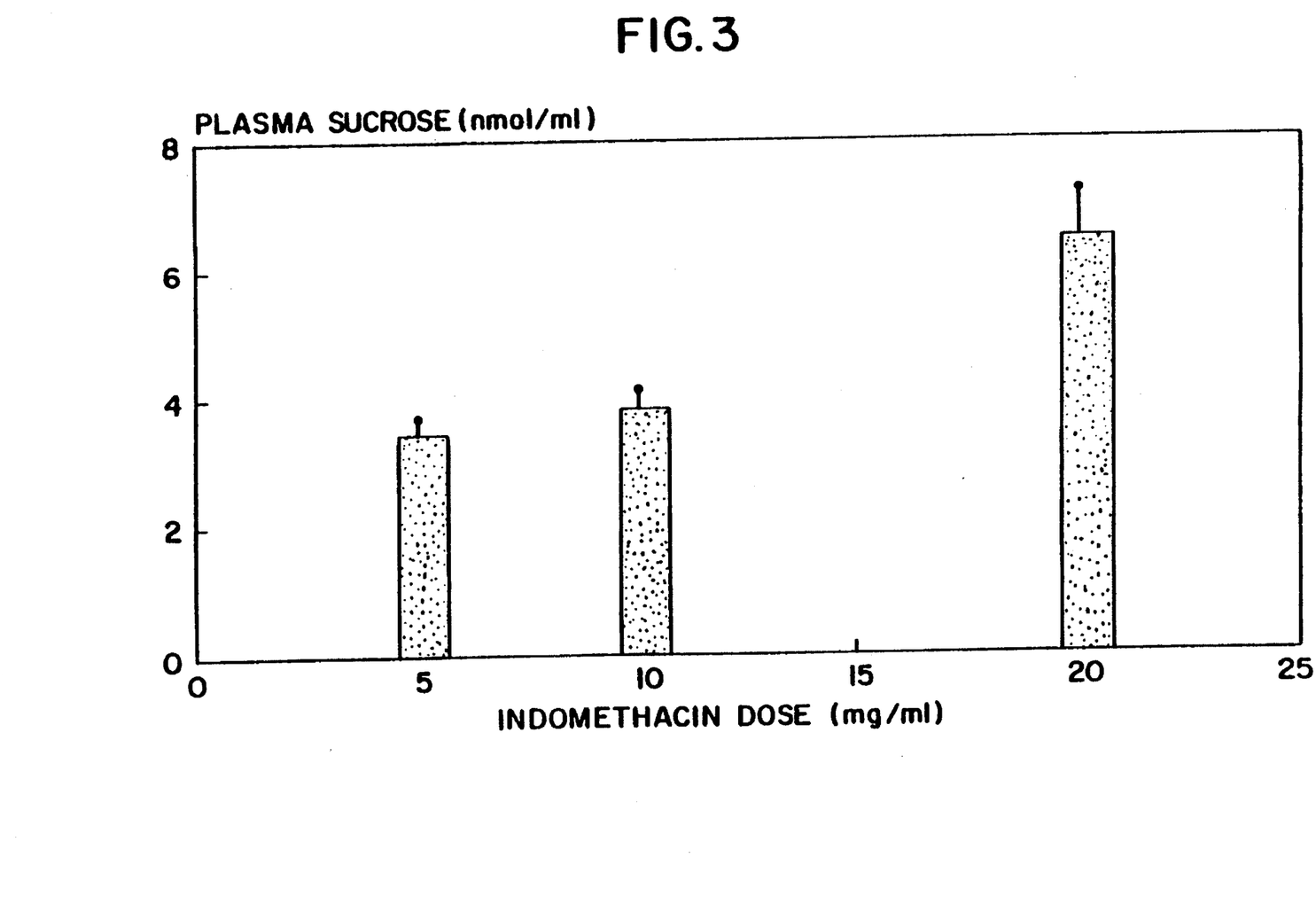
FIG. 3 is a graph of the plasma concentration of sucrose following a 60 minute gastric incubation of labeled sucrose for five to ten animals.

The experimental model in the rat was followed to induce epithelium damage. The rats were subsequently administered a sucrose solution which had been radiolabeled (5 mM). Five to ten animals were tested and the result of the experiment is shown in FIG. 3.

Figure 4:
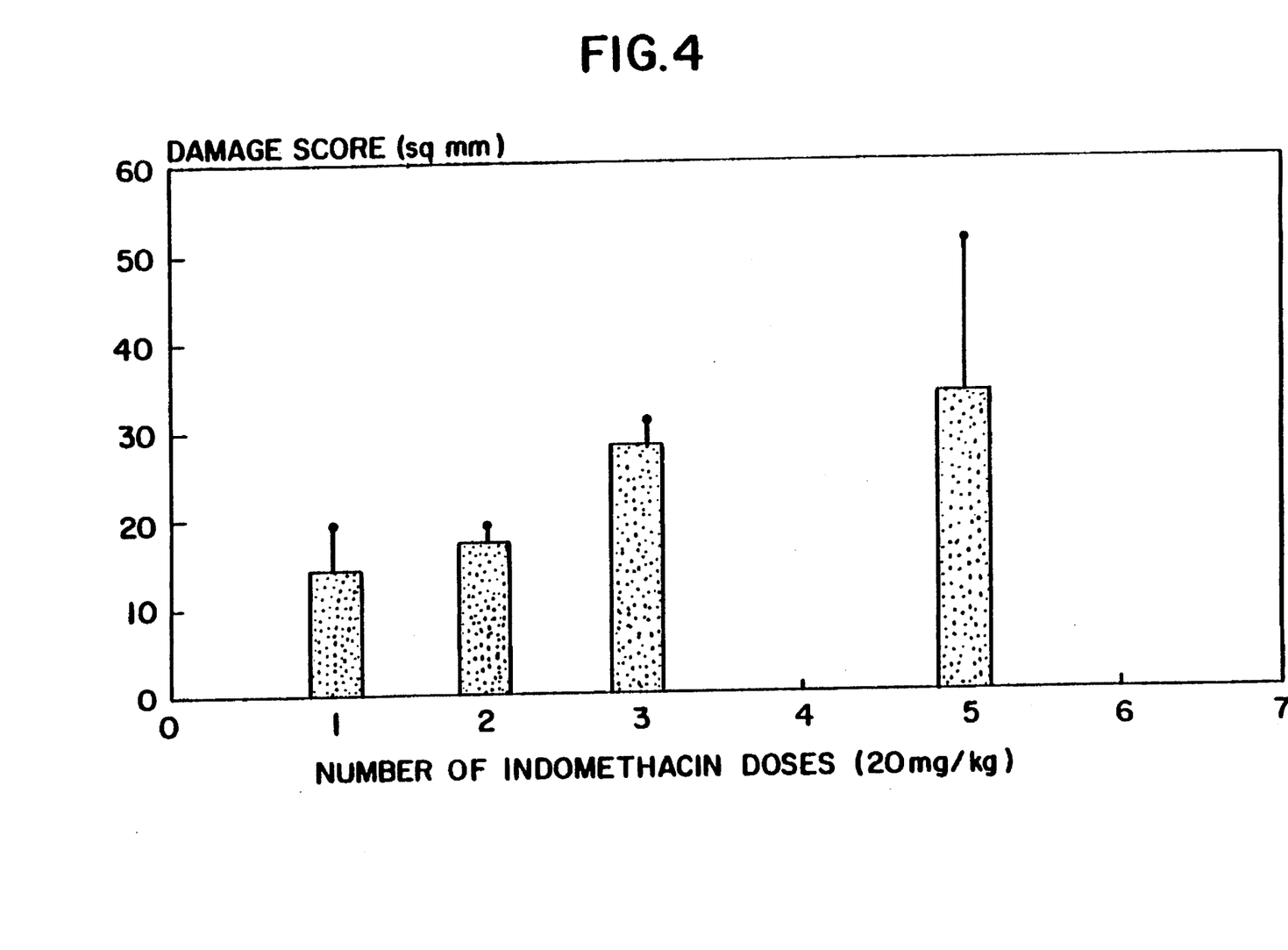
FIG. 4 is a graph representing gastric damage in rabbits receiving 20 mg/kg indomethacin scq 12 h.
Figure 5:
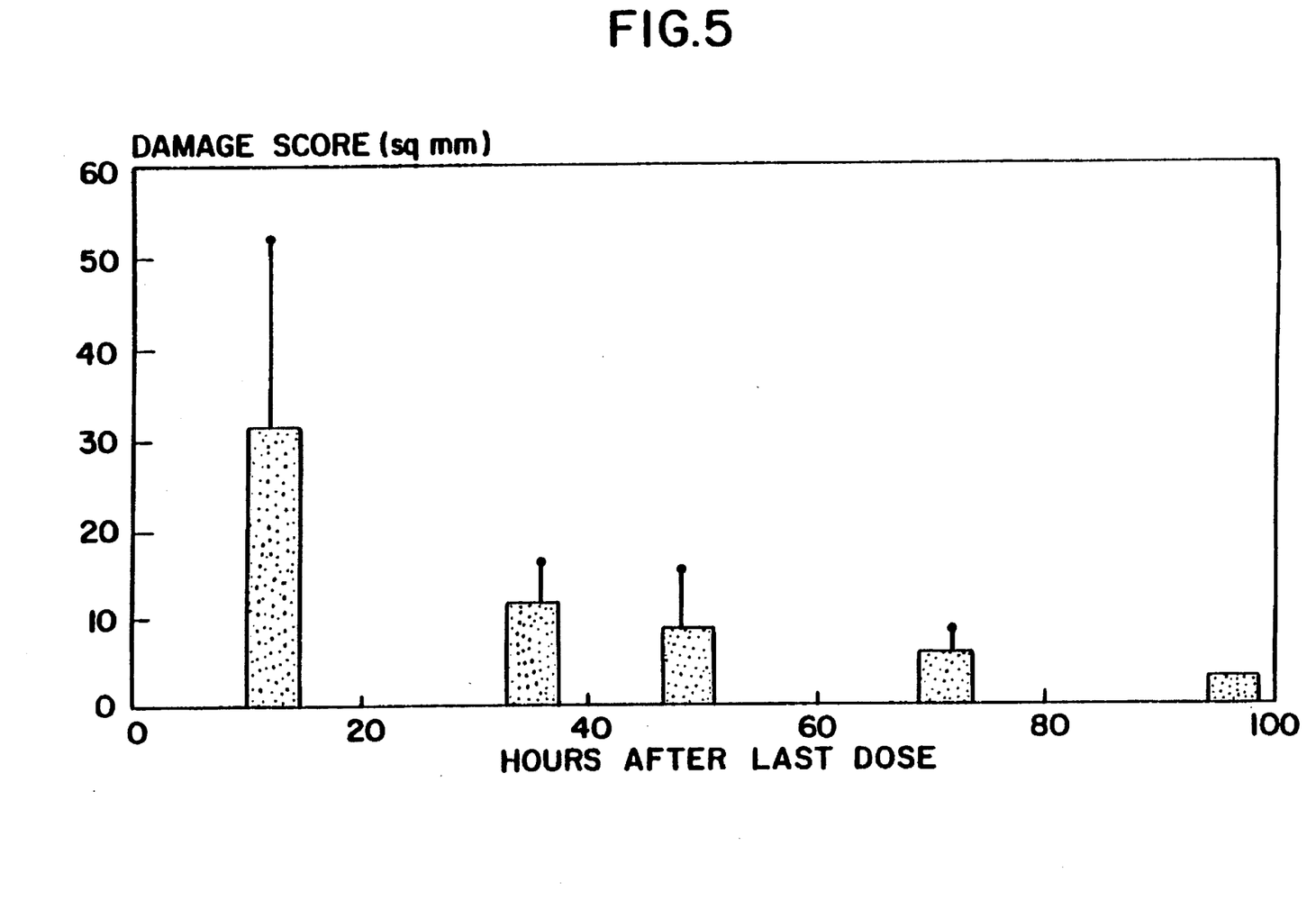
FIG. 5 is a graph illustrating gastric damage in rabbits which heals following induction with five consecutive doses of indomethacin wherein such data represents the mean ±SE 42–6 animals at each point.
Figure 6:
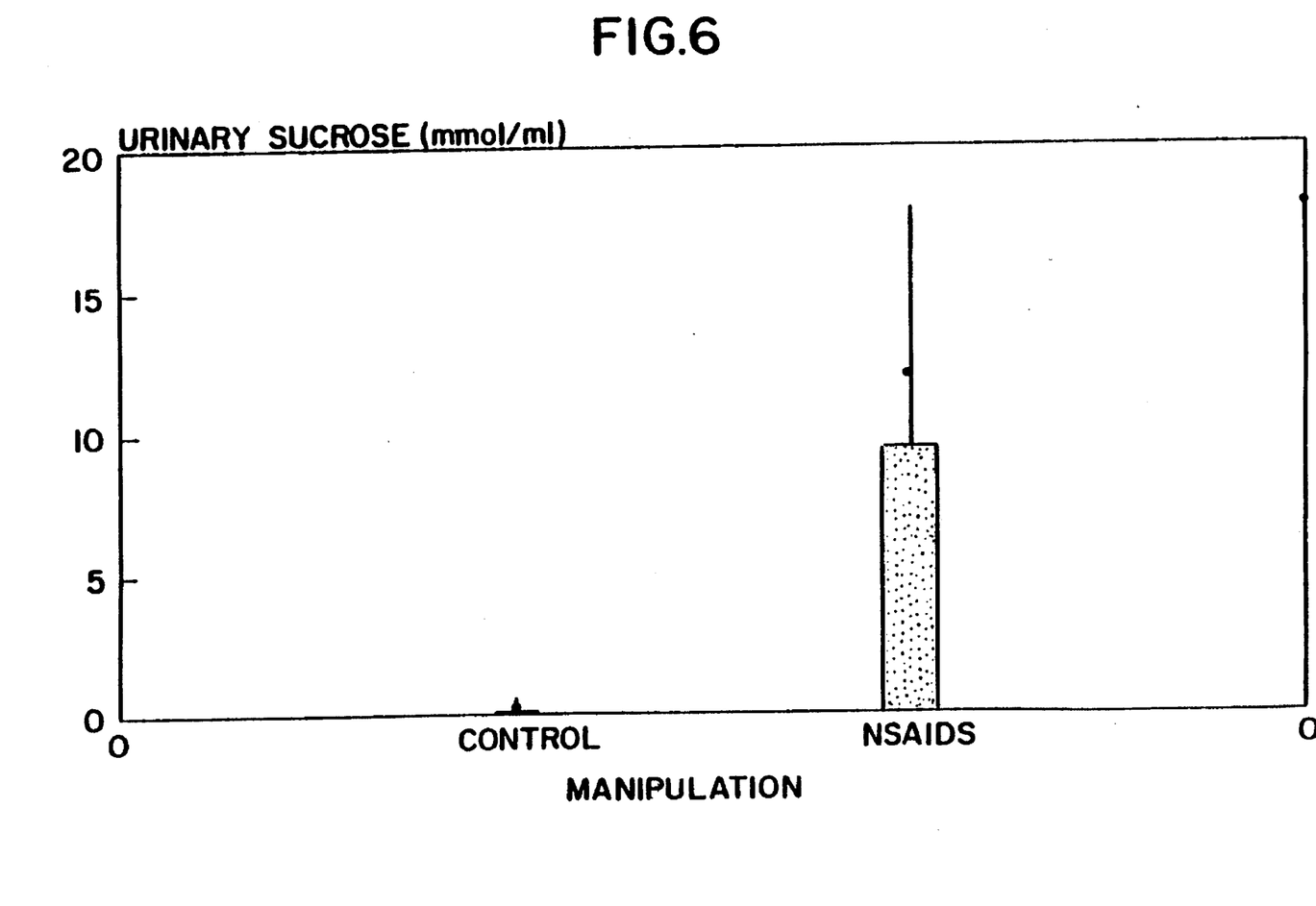
FIG. 6 is a graph representing the detection of NSAID-induced damage increase through increased urinary sucrose content following intra-gastric installation of labeled sucrose.

The data clearly shows that the sucrose was an acceptable indicator of NSAID-induced lesions in the stomach of the rats. The diagnostic methodology herein was further verified in a chronic NSAID-induced enteroulcer model in the rabbit. It was found that subcutaneous injection of indomethacin in rabbits produced lesions in the rabbit's stomach. Such damage appears in two distinct forms. FIG. 4 presents the degree of gastric damage quantitated as the surface area involved with superficial erosions following increasing numbers of indomethacin injections (20 milligrams/kg sc) at twelve hourly intervals. All animals were sacrificed twelve hours following the last dose and damage estimated as in the above-noted rat study. Superficial damage did occur but it was also noted that deep penetrating, chronic-appearing antral ulcerations occurred, some of which had perforated in animals receiving six or more consecutive doses. Such lesions are similar to those seen in man with NSAID-ingestion and appear to heal when the NSAIDs are withdrawn. As a further demonstration in the model, rabbits were administered five doses of sc indomethacin and then sacrificed at several time points following the final dose. FIG. 5 illustrates that the detected lesions are reversible in a time-dependent fashion. Following development of the animal model, rabbits were given seven doses of indomethacin or vehicle and, shortly after the last dose, anesthetized for the study. The stomach was catheterized at both the esophageal and pyloric ends and a solution containing 5 mM sucrose introduced for an hour. The detection methodology employed the use of [$^{14}$C]-sucrose within the test solution. The rabbit model enabled the collection of small amounts of urine produced over the course of the study which permitted the quantitative analysis for sucrose by scintillation counting. The results of the study are illustrated in FIG. 6. A much greater concentration of sucrose was found in the urine of animals with gastric damage following indomethacin administration. Urinary production rates were similar in both groups, thus the results represent increased urinary sucrose excretion in the NSAID-administered group.

The methodology herein was further validated in the following clinically-described trial using human subjects.

Human Clinical

Figure 7:
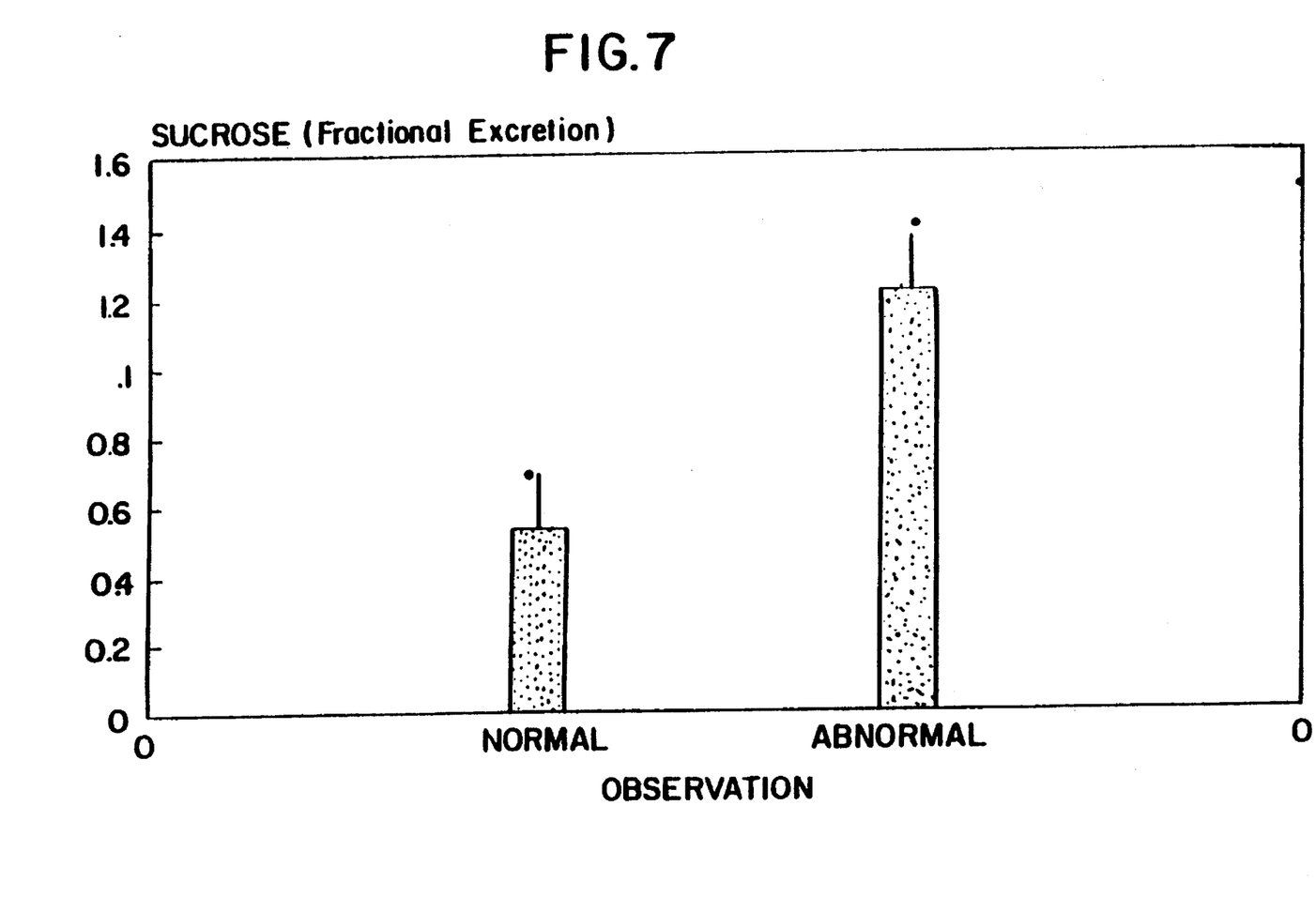
FIG. 7 is a graph representing fractional excretion of sucrose quantitated by HPLC in human urine following a sucrose-loading challenge.

In order to load patients with sucrose, a test meal was developed composed of a sucrose containing soft drink, Classic Coke (trademark of The Coca-Cola Company) and a sucrose containing candy bar, Mars candy bar (trademark of The M&M Mars Company) that delivered 105 grams of dietary sucrose. Patients were instructed to ingest this meal for breakfast following an overnight fast and then collect all urine for a five-hour period. Urine samples were brought in on the day of endoscopy and frozen. The patients had undergone endoscopies by gastroenterologists. The samples were evaluated using high performance liquid chromatography (HPLC) analysis. FIG. 7 presents the results of the study as the fraction of ingested sucrose excreted over the five-hour timed urine collection. As shown, measurable quantities of sucrose were found in the initial urine samples. In FIG. 7 it is shown that the patients were categorized as either a normal or abnormal endoscopy and it is apparent that in the latter group the fractional excretion of sucrose was greater than in the former. Abnormal endoscopies included macroscopically visible inflammation of the esophagus, stomach or duodenum as well as a small number of patients with apparently normal endoscopies but in whom antral biopsies revealed gastritis. The results show that the sucrose probe provided a sensitive methodology for the detection of lesions as the molecule exhibited that it could cross through regions of damage not necessarily visible to the eye.

The following human clinical trial was also performed to further evaluate the use of disaccharides as diagnostic agents for the detection of stomach epithelial damage.

Study Design

Ten individuals were recruited for a two-day test. On day one each individual fasted for an eight hour fast and ingested 500 ml. of an aqueous sucrose-containing drink containing 100 grams of sucrose. For the following five hours all urine was collected. Urine volume was recorded and sucrose concentration determined by HPLC. Total urinary sucrose excretion over the five hour period was calculated. On the second day each volunteer came to the laboratory and had the test repeated. However, prior to ingesting the sucrose drink, each patient took 650 mg. of acetylsalicylic acid (ASA). Fifteen minutes after ingesting the ASA (to allow maximal suppression of gastric prostaglandin production) 50 ml. of straight vodka was ingested. It is well documented that such ingestion of ASA and ethanol will produce acute superficial damage of the gastric mucosa and is similar to the experiments previously reported for the animal model. Five minutes later the sucrose was ingested and the five hour urine collection began. Table 1 illustrates the five hour urinary sucrose excretion for both days. Prior to the ingestion of ASA and alcohol, patients excreted 121.3±19.7 milligrams of sucrose. Following gastric damage, this value rose to 384±76.8 milligrams of sucrose, a highly significant difference. Although individual variation was present, gastric damage produced an increase in urinary sucrose excretion in all patients. As illustrated in Table 1, the variation was from 159% increase to a 996% increase in sucrose excretion following gastric damage. Average urinary sucrose excretion increased 3.53±0.78-fold following gastric damage.

Measurement of urinary sucrose excretion following an oral loading dose is a simple, well-tolerated and non-invasive technique for evaluation of gastric damage. Sucrose provides quantitative information regarding the degree of gastric damage.

TABLE 1

| PATIENT | DAY 1 (mg sucrose) | DAY 2 (mg sucrose) | FOLD INCREASE |
|---|---|---|---|
| 1 | 263.5 | 907 | 3.44 |
| 2 | 166.7 | 265 | 1.59 |
| 3 | 163.4 | 287.4 | 1.76 |
| 4 | 69 | 687 | 9.96 |
| 5 | 115 | 276 | 2.40 |
| 6 | 124 | 511 | 4.12 |
| 7 | 59 | 254 | 4.31 |
| 8 | 91 | 207 | 2.27 |
| 9 | 73.6 | 135 | 1.83 |
| 10 | 88 | 315 | 3.58 |
| MEAN | 121.32 | 384.44 | 3.53 |
| S.E.M. | 19.73 | 76.86 | 0.78 |

S.E.M. = Standard error of the mean value

What we claim is:

1. The use of a disaccharide as a diagnostic marker for indicating the existence or extent of gastric epithelial damage in a patient comprising orally administering to the patient a disaccharide, which does not transport across cell membranes, and which metabolizes to its monosaccharides in the lower intestine, and not in the stomach, and assaying the patient's blood or urine for the presence of the disaccharide to determine the existence or extent of gastric epithelial damage.

2. The diagnostic marker of claim 1 wherein the disaccharide is sucrose, maltose or lactose.

3. The diagnostic marker of claim 2 wherein the disaccharide is sucrose.

* * * * *

UNITED STATES PATENT AND TRADEMARK OFFICE
CERTIFICATE OF CORRECTION

PATENT NO. : 5,605,840

DATED : February 25, 1997

INVENTOR(S) : J. MEDDINGS ET AL.

It is certified that error appears in the above-identified patent and that said Letters Patent is hereby corrected as shown below:

On the title page,

Item [30] Foreign Application Priority Data

Insert: --Sep. 17, 1992 PCT/CA92/00402--.

Signed and Sealed this

Twenty-first Day of April, 1998

Attest:

BRUCE LEHMAN

*Attesting Officer*  *Commissioner of Patents and Trademarks*